(12) United States Patent
Hansson et al.

(10) Patent No.: US 10,124,328 B2
(45) Date of Patent: *Nov. 13, 2018

(54) SEPARATION METHOD AND SEPARATION MATRIX

(71) Applicant: GE Healthcare BioProcess R&D AB, Uppsala (SE)

(72) Inventors: Jesper Hansson, Uppsala (SE); Gustav Rodrigo, Uppsala (SE); Tobias E Soderman, Uppsala (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 25 days.

This patent is subject to a terminal disclaimer.

(21) Appl. No.: 15/407,240

(22) Filed: Jan. 16, 2017

(65) Prior Publication Data

US 2017/0120232 A1  May 4, 2017

Related U.S. Application Data

(63) Continuation of application No. 14/396,207, filed as application No. PCT/SE2013/050427 on Apr. 22, 2013, now Pat. No. 9,573,973.

(30) Foreign Application Priority Data

Apr. 25, 2012 (SE) ...................... 1250413

(51) Int. Cl.
| | | |
|---|---|---|
| *B01J 39/26* | (2006.01) | |
| *B01D 15/18* | (2006.01) | |
| *B01D 15/36* | (2006.01) | |
| *B01J 20/286* | (2006.01) | |
| *B01J 20/32* | (2006.01) | |
| *B01D 15/38* | (2006.01) | |
| *B01J 20/26* | (2006.01) | |
| *B01J 20/28* | (2006.01) | |
| *B01J 20/289* | (2006.01) | |
| *B01J 20/30* | (2006.01) | |
| *C07H 1/08* | (2006.01) | |
| *C07K 1/22* | (2006.01) | |
| *B01D 15/34* | (2006.01) | |
| *B01J 20/24* | (2006.01) | |
| *G01N 30/88* | (2006.01) | |

(52) U.S. Cl.
CPC .......... *B01J 39/26* (2013.01); *B01D 15/1864* (2013.01); *B01D 15/34* (2013.01); *B01D 15/361* (2013.01); *B01D 15/362* (2013.01); *B01D 15/3809* (2013.01); *B01J 20/24* (2013.01); *B01J 20/261* (2013.01); *B01J 20/265* (2013.01); *B01J 20/267* (2013.01); *B01J 20/286* (2013.01); *B01J 20/289* (2013.01); *B01J 20/28014* (2013.01); *B01J 20/28033* (2013.01); *B01J 20/3085* (2013.01); *B01J 20/3212* (2013.01); *B01J 20/3278* (2013.01); *B01J 20/3282* (2013.01); *C07H 1/08* (2013.01); *C07K 1/22* (2013.01); *B01J 2220/80* (2013.01); *G01N 2030/8827* (2013.01); *Y02P 20/582* (2015.11)

(58) Field of Classification Search
CPC .............. B01D 15/1864; B01D 15/361; B01D 15/3809; B01J 20/286; B01J 20/289; B01J 20/3212; B01J 20/3278; C07K 1/22
USPC ........... 526/263, 278; 530/344, 387.1, 387.3, 530/391.1, 413; 536/25.4
See application file for complete search history.

(56) References Cited

U.S. PATENT DOCUMENTS

| | | | |
|---|---|---|---|
| 5,453,186 A | 9/1995 | Mueller et al. | |
| 6,322,695 B1 | 11/2001 | Lee et al. | |
| 7,691,263 B1 | 4/2010 | Gu et al. | |
| 9,573,973 B2 * | 2/2017 | Hansson ............ | B01D 15/1864 |
| 2002/0104801 A1 | 8/2002 | Voute et al. | |
| 2010/0181254 A1 | 7/2010 | Graalfs | |
| 2011/0117626 A1 | 5/2011 | Komkova et al. | |
| 2012/0029154 A1 | 2/2012 | Deetz et al. | |

FOREIGN PATENT DOCUMENTS

| | | |
|---|---|---|
| EP | 0337144 A1 | 10/1989 |
| EP | 1071500 B1 | 3/2005 |
| EP | 1091981 B1 | 8/2007 |
| EP | 2412433 A2 | 2/2012 |
| EP | 2499192 A1 | 9/2012 |
| EP | 2152405 B1 | 10/2012 |
| JP | 1310744 A | 12/1989 |
| JP | 2002510787 A | 4/2002 |
| JP | 2009215566 A | 9/2009 |
| JP | 2010528271 A | 8/2010 |

(Continued)

OTHER PUBLICATIONS

Zouahri et al., European Polymer Journal 38, 2002, pp. 2247-2254.

(Continued)

*Primary Examiner* — Edward J Cain
(74) *Attorney, Agent, or Firm* — Wood IP LLC

(57) ABSTRACT

The invention discloses a method of separating a biomolecule from at least one other component in a liquid, comprising a step of contacting said liquid with a separation matrix comprising a solid support and polymer chains bound to said solid support. The polymer chains comprise units derived from a first monomer of structure $CH_2=CH-L-X$, where L is a covalent bond or an alkyl ether or hydroxy-substituted alkyl ether chain comprising 2-6 carbon atoms, and X is a sulfonate or phosphonate group.

20 Claims, 12 Drawing Sheets

(56) References Cited

FOREIGN PATENT DOCUMENTS

| | | |
|---|---|---|
| JP | 2012032392 A | 2/2012 |
| JP | 2013510918 A | 3/2013 |
| WO | 1999/051316 A1 | 10/1999 |
| WO | 1999/064480 A1 | 12/1999 |
| WO | 1999064480 | 12/1999 |
| WO | 2008/145270 A1 | 12/2008 |
| WO | 2011/058439 A1 | 5/2011 |
| WO | 2011058439 | 5/2011 |

OTHER PUBLICATIONS

PCT/SE2013/050427 PCT ISRWO dated Jul. 26, 2013.
Zouahri et al. "Synthesis of Ion Exchange Membranes From Ozonized High Density Polyethylene", European polymer Journal, vol. 38, 2002, pp. 2247-2254.
Office Action Received received for Japanese Patent Application No. 2015-508919, dated Mar. 14, 2017, 3 pages. (Official copy only).

\* cited by examiner

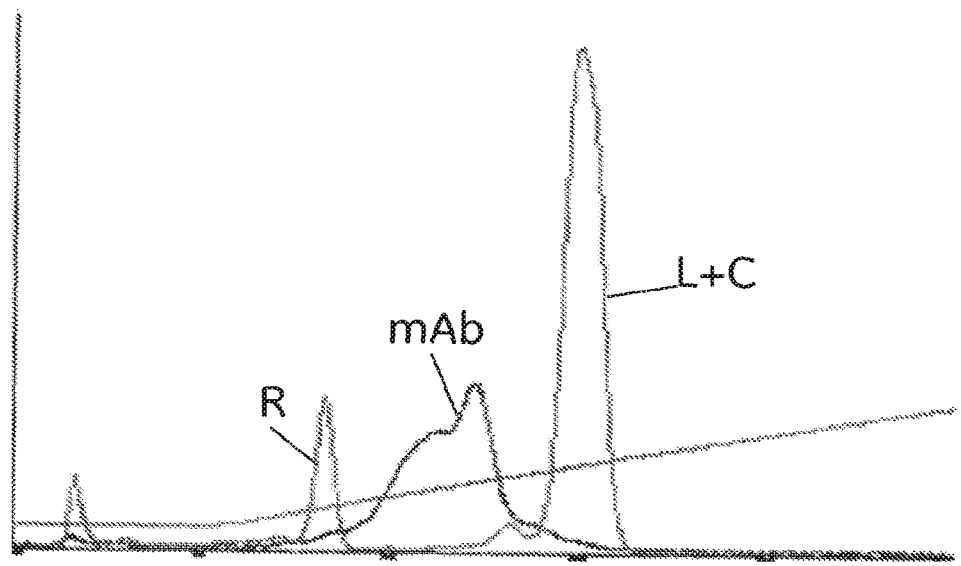
a)
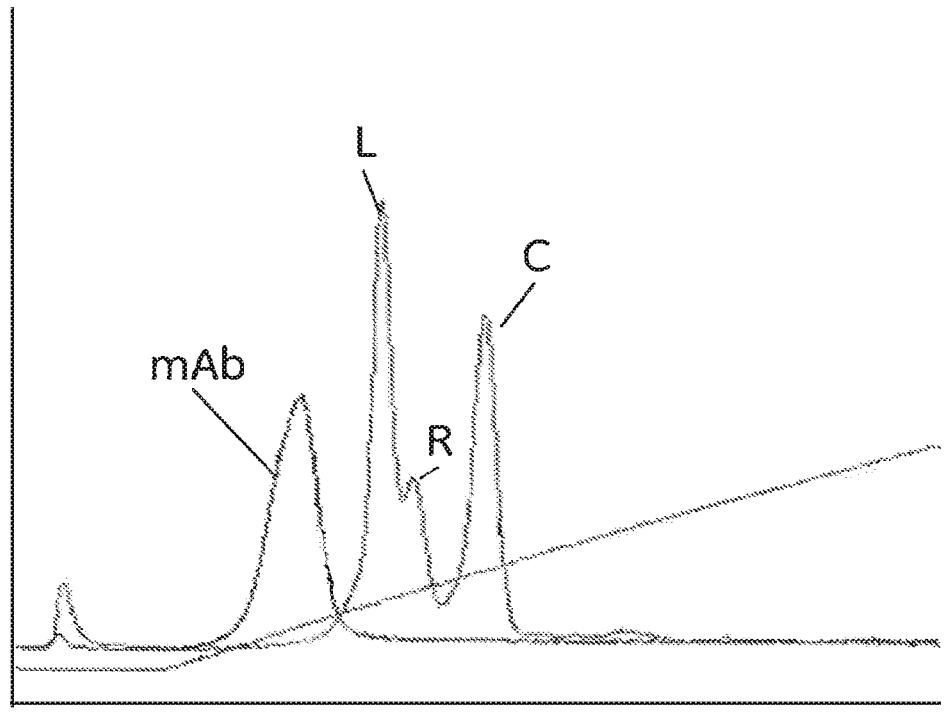
b)                Figure 13

SEPARATION METHOD AND SEPARATION MATRIX

TECHNICAL FIELD OF THE INVENTION

The present invention relates to separation of biomolecules, and more particularly to ion exchange separation of proteins. The invention also relates to a separation matrix suitable for separation of biomolecules and to a method of manufacturing such a matrix.

BACKGROUND OF THE INVENTION

There are many instances when it is required to separate one compound such as a contaminant or a desired molecule, from a liquid. Charge-charge based interactions are used in a number of fields to capture and hence separate charged or chargeable compounds.

In the chemical and biotech field, target compounds such as drug or drug candidates usually need to be separated from contaminating species originating from the process of manufacture. For example, a protein drug or drug candidate produced by expression of recombinant host cells will need to be separated e.g. from the host cells and possibly cell debris, other host cell proteins, DNA, RNA, and any other compounds originating from the fermentation or cell culture broth. Due to its versatility and sensitivity to the target compounds, chromatography is involved as at least one step in many of the currently used biotech purification schemes. The term chromatography embraces a family of closely related separation methods which are all based on the principle that two mutually immiscible phases are brought into contact. More specifically, the target compound is introduced into a mobile phase, which is contacted with a stationary phase. The target compound will then undergo a series of interactions between the stationary and mobile phases as it is being carried through the system by the mobile phase. The interactions exploit differences in the physical or chemical properties of the components of the sample.

The stationary phase in chromatography is comprised of a solid carrier to which ligands, which are functional groups capable of interaction with the target compound, have been coupled. Consequently, the ligands will impart to the carrier the ability to effect the separation, identification, and/or purification of molecules of interest. Liquid chromatography methods are commonly named after the interaction principle utilized to separate compounds. For example, ion exchange chromatography is based on charge-charge interactions; hydrophobic interaction chromatography (HIC) utilizes hydrophobic interactions; and affinity chromatography is based on specific biological affinities.

As is well known, ion exchange is based on the reversible interaction between a charged target compound and an oppositely charged chromatography matrix. The elution is most commonly performed by increasing the salt concentration, but changing the pH is equally possible. Ion-exchangers are divided into cation-exchangers, wherein a negatively charged chromatography matrix is used to adsorb a positively charged target compound; and anion-exchangers, wherein a positively charged chromatography matrix is used to adsorb a negatively charged target compound. The term "strong" ion exchanger is used for an ion-exchanger which is charged over broad pH intervals, while a "weak" ion-exchanger is chargeable at certain pH values. One commonly used strong cation-exchanger comprises sulphonate ligands, known as S groups. In some cases, such cation exchangers are named by the group formed by the functional group and its linker to the carrier; for example SP cation exchangers wherein the S groups are linked by propyl to the carrier.

The charged groups in ion exchangers (often called ligands) can be attached to the carriers or support materials in different ways. Several publications (U.S. Pat. No. 5,453,186, WO2008145270, U.S. Pat. No. 8,092,682, WO2012015379, EP2412433 and EP2412435) describe how charged monomers can be graft polymerized on support materials to form ion exchangers where the ligands are present on pendant graft polymer chains covalently attached to the supports. However, in particular in the bioprocessing area, the demands on the separation matrices are continuously increasing and there is hence a need for further developments, particularly with respect to matrices providing improved selectivity and capacity, as well as stability during alkaline cleaning.

SUMMARY OF THE INVENTION

One aspect of the invention is to provide a separation method with high throughput and high selectivity. This is achieved with a method as defined in claim 1. One advantage is that a high binding capacity for target proteins can be achieved, in combination with a high selectivity between e.g. monomeric and aggregated immunoglobulins. Further advantages are that high binding capacities at elevated ionic strengths, rapid mass transport/binding kinetics and high alkali stabilities—allowing a large number of cycles to be performed before the matrix has to be exchanged—can be achieved.

Another aspect of the invention is to provide a separation matrix with high binding capacity and high selectivity for target proteins, as well as a high alkali stability This is achieved with a matrix
  comprising a solid support and copolymer chains bound to said solid support, wherein said copolymer chains comprise units derived from
  a) a first monomer selected from a group consisting of vinyl sulfonate and allyloxyhydroxypropyl sulfonate and
  b) a second non-charged monomer selected from the group consisting of N-vinyl pyrrolidone, N-vinyl caprolactam, N-vinyl formamide and N-vinyl acetamide,
  wherein in said copolymer chains the molar ratio of the units derived from the first monomer to the units derived from the second non-charged monomer is 0.5 to 2 and
  wherein the total content of said copolymer chains in the matrix is 2-20 mg/ml.

A third aspect of the invention is to provide a method of manufacturing a separation matrix described herein with high binding capacity and high selectivity fix target proteins, as well as a high alkali stability. This is achieved with a method
  comprising the steps of:
  a) providing a solid support comprising moieties with copolymerizable C=C double bonds or moieties susceptible to formation of free radicals;
  b) contacting the solid support with a mixture comprising the first and second monomer and;
  c) initiating radical polymerization.

Further suitable embodiments of the invention are described in the dependent claims.

BRIEF DESCRIPTION OF THE FIGURES

FIG. 13 shows chromatograms for a protein mixture and a monoclonal antibody on a) the reference matrix SP Sepharose HP and b) a VPA-grafted matrix of the invention.

DETAIL DESCRIPTION OF EMBODIMENTS

Figure 1:
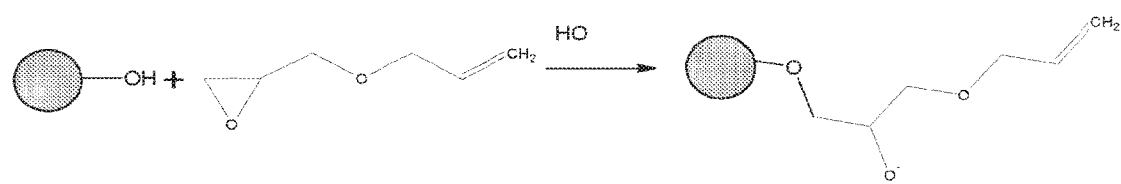
FIG. 1 shows the reaction scheme for allylation of hydroxyl groups on a support allyl glycidyl ether.

In one aspect the present invention discloses a method of separating biomolecule from at least one other component in a liquid. The method comprises a step of contacting the liquid with a separation matrix, which comprises a solid support and polymer chains bound to the solid support, wherein the polymer chains comprise units derived from a first monomer of structure $CH_2=CH-L-X$, where L is i) a covalent bond or ii) an alkyl ether or hydroxysubstituted alkyl ether chain, either of which comprises 2-6 carbon atoms, and X is a sulfonate or phosphonate group. The structure of these units in the polymer chains will be:

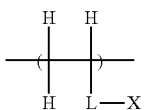

The biomolecule can be dissolved in the liquid and the other component(s) can also be dissolved in the liquid. The contacting step can e.g. take place by conveying the liquid through a column, a membrane adsorber or other device packed with the separation matrix, but it can also be carried out by e.g. batch adsorption where matrix and liquid are mixed in a container. The separation can occur through adsorption of the biomolecule or of the other component(s) to the matrix. The pH in the contacting step may e.g. be 1-7, such as 4.5-6 or 4.75-5.5 and the ionic strength may be e.g. 10-100 mM, such as 20-60 mM. The liquid may be an aqueous buffer and may comprise a buffering component such as acetate, phosphates, citrates, succinates etc. and a salt such as an alkali chloride, an alkali sulfate, ammonium sulfate etc. It may also comprise additives such as detergents, amino acids, water-miscible solvents, water soluble polymers, chaotropes, cosmotropes etc.

In certain embodiments the biomolecule is a biomacromolecule, such as protein, a peptide or a nucleic acid. Examples of suitable proteins include plasma proteins, immunoglobulins and recombinant proteins like e.g. erythropoietin, interferons, blood coagulation factors etc., while examples of peptides can be insulin etc. The biomolecule can also be a vaccine antigen, including virus particles, virus proteins, bacterial polysaccharides and bacterial proteins.

In some embodiments the biomolecule is an immunoglobulin, immunoglobulin fragment or an immunoglobulin-containing protein, such as an antibody, an antibody fragment, an antibody conjugate or an antibody fusion protein. Immunoglobulins, as well as fragments and immunoglobulin fusion proteins is an important class of biopharmaceuticals and the method of the invention is particularly suitable for removal of contaminants from these substances.

In certain embodiments said at least other component is a protein, such as a host cell protein, Protein A or an aggregate of immunoglobulins, immunoglobulin fragments or immunoglobulin-containing proteins. Examples of aggregates can be e.g. dimers, trimers and/or higher multimers. The method of the invention is particularly suitable for protein-protein separations, such as removal of host cell proteins, Protein A, aggregates, charge variants, misfolded proteins etc. from immunoglobulins and related substances. Efficient clearance of these contaminants is essential in the production of biopharmaceuticals, as they can cause immunogenicity and other undesirable side effects. The other component can also be e.g. antibiotics added during cell culture, endotoxins, viruses or solvents and detergents added for inactivation of viruses. The other component can further be a reactant used to form a conjugate, such as e.g. the drug component of an antibody-drug conjugate or PEG in the case of a PEG-ylated protein.

In some embodiments the liquid is an eluate from a previous chromatography step, such as an affinity step, an ion exchange step, a multimodal step or a hydrophobic interaction step. The method of the invention is particularly suitable for removal of residual contaminants present in e.g. protein solutions eluted form a previous chromatography step. The previous step can be a capture step such as e.g. a protein A or a protein L chromatography step and the residual contaminants may be e.g. host cell proteins, aggregates, leached protein A or L or viruses.

In certain embodiments the liquid is the flow-through from a separation matrix, such as an ion exchange matrix, a multimodal matrix or a hydrophobic interaction matrix. The method can e.g. be applied after a previous flow-through chromatography step, such as an anion exchange or multimodal anion exchange flow-through step applied after a protein A step in an antibody process.

In some embodiments said biomolecule is an immunoglobulin, immunoglobulin fragment or an immunoglobulin-containing protein, such as an antibody, an antibody fragment, an antibody conjugate or an antibody fusion protein and wherein at least 1%, such as at least 5% or at least 10% of said biomolecule is in the form of aggregates, such as dimers, trimers and higher multimers. The method is particularly useful for removal of aggregates, which can be produced either during cell cultivation or during processing e.g. when the immunoglobulins are exposed to low pH during elution of a protein A column or during virus inactivation.

In certain embodiments the method further comprises a step of eluting said biomolecule from said separation matrix with an elution buffer. The method of the invention may be carried out in bind-elute mode, in which case the biomolecule is adsorbed to the matrix and afterwards eluted with the elution buffer. The other component(s) may pass through the matrix in the flow-through or they may bind to some extent and be eluted separately from the biomolecule. The elution can be performed as a step change in buffer composition or pH, a series of step changes or by a gradient in buffer composition or pH. The method can also comprise a washing step with a washing buffer. This step serves the purpose of removing non-bound or loosely bound other components and can e.g. be applied after the contacting step and before the elution step. Elution and wash buffers may comprise buffering substances such as acetate, phosphates, citrates, succinates, Tris, glycine etc. They may also comprise neutral salts, lyotropic salts, detergents, amino acids, water-miscible solvents, water soluble polymers, chaotropes, cosmotropes and other additives.

The method may also be applied in flow-through mode, where the other component(s) adsorb to the matrix, while the biomolecule does not adsorb or adsorbs very weakly and can be recovered in purified form in the flow-through. The adsorbed other component(s) may then be removed by a strip buffer applied to the matrix.

In some embodiments the method further comprises a step of cleaning said separation matrix with a cleaning liquid. The cleaning liquid can be an alkaline cleaning liquid comprising at least 0.1 mol/l of an alkali hydroxide such as NaOH or KOH. It can e.g. be a 0.5-2 mol/l NaOH or KOH solution, such as an aqueous solution of about 1 M NaOH. In addition to the alkali hydroxide, the solution may also comprise chaotropic agents, solvents, detergents, salts etc. to improve the cleaning efficiency. It is a particular advantage of the method of the invention that alkaline cleaning can be used without causing degradation to the matrix. The method, including the cleaning step with an alkaline cleaning liquid (e.g. 1 M NaOH) can be repeated many times, such as at least 10, at least 50, 10-100 or 50-100 times. This allows for repeated use of the matrix over a large number of cycles, which is important for a good process economy.

The method may also comprise further subsequent separation steps. It may e.g. be followed by one or more chromatography steps, such as anion exchange, cation exchange, multimodal, hydroxyapatite, hydrophobic interaction or size exclusion chromatography. It can also be followed by membrane filtration, e.g. ultrafiltration.

In certain embodiments, the polymer chains are copolymer chains and further comprise units derived from a second non-charged monomer. The copolymer chains can e.g. be random copolymer chains or they can have an alternating or segmented structure. An advantage of having the non-charged units in the chains is that the local charge density of the chains can be controlled, which enables improvements in binding capacity and selectivity. Through the incorporation of a non-charged comonomer it may also be possible to increase the incorporation of sluggishly polymerizing charged comonomers during manufacture of the matrix.

In some embodiments, the second non-charged monomer is an N-vinylamide. The n-vinylamide can e.g. be selected from the group consisting of N-vinyl pyrrolidone, N-vinyl caprolactam, N-vinyl formamide and N-vinyl acetamide. These monomers provide advantageous chain structures in combination with the $CH_2=CH-L-X$ monomers and the polymers are highly resistant against alkaline degradation, In some embodiments, L is a covalent bond or —$CH_2$—O-L'—, where L' is a $C_2$-$C_4$ or $C_3$-$C_4$ alkylene chain, optionally substituted with at least one hydroxyl group. When L is a covalent bond, X will be directly linked to the $CH_2$=CH group (and hence to the backbone chain in the polymer) and when L is —$CH_2$—O-L'—, the monomer will be an allyl ether. These structures are free of carbonyls and give polymers with excellent alkali stability. It also appears that the polymers formed are favorable for providing good selectivities and binding capacities.

In certain embodiments, the first monomer is selected from the group consisting of vinyl sulfonate, vinyl phosphonate and allyloxyhydroxypropyl sulfonate. In some embodiments, the first monomer is selected from this group, or is vinyl sulfonate, and the second monomer is an N-vinyl amide, such as N-vinyl pyrrolidone. The combinations of these monomers give particularly alkali stable polymers and the monomers show favorable copolymerization behavior, such that matrices with suitable amounts of grafted polymer and suitable ionic capacities can be prepared.

In some embodiments, in said copolymer chains the molar ratio of the units derived from the first monomer to the units derived from the second monomer is 0.05 to 5, such as 0.10 to 2 or 0.5 to 2.

In certain embodiments, the polymer or copolymer chains are bound to the support by linker units derived from allyl ethers, such as e.g. allyl hydroxypropyl ethers.

In one aspect the present invention discloses a separation matrix comprising a solid support and copolymer chains bound to the solid support, wherein the copolymer chains comprise units derived from a) a first monomer of structure $CH_2$=CH-L-X, where L is a covalent bond or an alkyl ether or hydroxysubstituted alkyl ether chain comprising 2-6 carbon atoms, and X is a sulfonate or phosphonate group and b) a second non-charged monomer.

The copolymer chains may be grafted to the solid support, with one or more links to the support for each chain. The chains may e.g. consist essentially of the first and second monomer units but they can also comprise other monomer units. The copolymer chains can have a random structure but they can also be alternating or segmented. The embodiments of the matrix of the invention are suitable for use in the separation methods described above.

In certain embodiments L is a covalent bond or —$CH_2$—O-L'-, where L' is a $C_2$-$C_4$ or $C_3$-$C_4$ alkylene chain, optionally substituted with at least one hydroxyl group. As described above these structures provide high alkali resistance and are beneficial for providing high capacities and selectivities.

In some embodiments the charged monomer is selected from the group consisting of vinyl sulfonate, vinyl phosphonate and allyloxyhydroxypropyl sulfonate. These commercially available monomers are suitable for grafting and provide good capacities/selectivities as well as alkali stability.

In certain embodiments said second non-charged monomer is an N-vinyl amide, N-vinyl amides copolymerize well with the charged monomers and give remarkably alkali-resistant polymers. This applies in particular to cyclic N-vinyl amides (e.g. N-vinyl lactams).

In some embodiments said second non-charged monomer is selected from the group consisting of N-vinyl pyrrolidone, N-vinyl caprolactam, N-vinyl formamide and N-vinyl acetamide. In some embodiments, the first monomer is selected from this group, or is vinyl sulfonate, and the second monomer is an N-vinyl amide, such as N-vinyl pyrrolidone. The combinations of these monomers give particularly alkali stable polymers and the monomers show favorable copolymerization behavior, such that matrices with suitable amounts of grafted polymer, suitable compositions of the grafted polymer and suitable ionic capacities can be prepared. The alkali stability of these copolymers is higher than for acrylamide or (meth)acrylate polymers, as described e.g. in US20100181254, and although monomers like vinyl sulfonate are generally considered slow or difficult to polymerize, our results show that the graft polymerizations work surprisingly well and that they copolymerize efficiently with e.g. vinyl pyrrolidone, to produce grafted matrices with high alkali stability and good chromatographic properties.

In certain embodiments in said copolymer chains the molar ratio of the units derived from the first monomer to the units derived from the second monomer is 0.05 to 5, such as 0.10 to 2 or 0.5 to 2. The molar ratio can be determined by spectroscopic methods and it can also be calculated from the ion capacity and the total content of copolymer chains (see below). If sulfur or phosphorus is only present in the first monomer and nitrogen is only present in the second monomer, the molar ration can also be determined from elemental analysis data.

In some embodiments the (hydrogen) ion capacity of the matrix is 15-300 or 20-300 micromol/ml, such as 70-300, 20-200, 20-80 or 30-70 micromol/ml. The hydrogen ion capacity can be determined by well-known titration methods. If sulfur or phosphorus is only present in the acidic groups, the ion capacity can also be calculated from elemental analysis data. Ionic capacities around 30-70 micromol/ml can provide both high protein capacities and high monomer-aggregate selectivities, but it is also possible to use ion capacities up to at least 200 micromol/ml, particularly when high protein capacities are desired.

The total content of (co)polymer chains in the matrix may be 2-80 or 2-60 mg/ml, such as 4-35, 4-20, 3-12, 12-20, 20-80 or 25-75 mg/ml. This can be determined by spectroscopic methods, by elementary analysis (depending on the monomers used) and as the weight add-on during preparation of the matrix. A relatively low content (e.g. 2-20 mg/ml) is advantageous for the monomer-aggregate selectivity, while a higher content (e.g. 20-80 mg/ml) can provide for higher protein binding capacities.

In certain embodiments, the polymer or copolymer chains are bound to the support by linker units derived from allyl ethers, such as e.g. allyl hydroxypropyl ethers. The chains may be bound by one or more such linker units per chain.

In certain embodiments the solid support comprises a polyhydroxy polymer, such as a polysaccharide. Examples of polysaccharides include agar, agarose, carrageenan, dextran, cellulose, pullulan etc. and examples of other polyhydroxy polymers include polyvinyl alcohol, polyglycidol etc. Advantages of polyhydroxy polymer supports include their hydrophilicity (which can eliminate or reduce non-specific interactions), their alkali stability and their propensity to forming porous structures with large surface areas and rapid mass transport.

In some embodiments the solid support comprises agar or agarose in native or derivatized form. These polysaccharides from large-pore gels with good mechanical properties and good mass transport properties for use in bioseparation. Agarose supports in bead form are commercially available e.g under the trade names of Sepharose and Capto (GE Healthcare Bio-Sciences AB) and they can be prepared e.g. as described in Hjertén et al (Biochim Biophys Acta 79, 393-398 (1964)). The pore size of the supports can be controlled by the concentration of the agarose solution used to manufacture them and to some extent by the crosslinking conditions. The particle size of the beads can be controlled by the input of mechanical energy during emulsion (or aerosol) formation and it is also possible to prepare fractions of polydisperse bead materials by sieving In certain embodiments the solid support is crosslinked, such as with hydroxyalkyl ether crosslinks. Crosslinking improves rigidity and chemical stability and an advantage of using hydroxyalkyl ether crosslinks is that they are alkali stable and do not cause non-specific interactions with proteins. Such crosslinks can be produced e.g. by the use of epihatohydrins, diepoxides and allyl halides/allyl glycidyl ethers as crosslinking reagents. Crosslinked agarose of high rigidity, prepared e.g. by the methods described in U.S. Pat. No. 6,602,990 or U.S. Pat. No. 7,396,467 can advantageously be used as a solid support.

In some embodiments the solid support is porous, such as in the form of porous beads or a porous membrane.

In certain embodiments the solid support has a pore size corresponding to a $K_d$ value of 0.5-0.9, such as 0.6-0.8, measured with dextran of Mw 110 kDa as the probe molecule. The pore size has importance for the capacity but also for the selectivity. In swelling materials like agarose and other polysaccharide gels, the pore size is best estimated by an inverse size exclusion chromatography method, where the volume fraction $K_d$ accessible for a probe molecule, e.g. dextran of Mw 110 kDa, is determined. This method is described in e.g. L Hagel et al: J Chromatogr A 743, 33-42 (1996).

In some embodiments the separation matrix has a pore size corresponding to a $K_d$ value of 0.1-0.8, such as 0.2-0.6 or 0.2-0.4, measured with dextran of Mw 110 kDa as the probe molecule. The Kd value is by definition a value between 0 and 1 and since material has been added to the solid support by the grafting, in most cases the Kd value of the matrix (with the grafted polymer) will be lower than the corresponding value for the solid support before grafting. Kd values between 0.2 and 0.6 or 0.2 and 0.4 provide god aggregate removal in combination with a high capacity.

In one aspect the present invention discloses a method of manufacturing a separation matrix according to any one of the embodiments described above, comprising the steps of:
a) providing a solid support comprising moieties with copolymerizable C=C double bonds or moieties susceptible to formation of free radicals;
b) contacting the solid support with a mixture comprising the first and second monomer and;
c) initiating radical polymerization.

The support may inherently comprise double bonds (e.g. residual double bonds on methacrylate or styrene-divinylbenzene supports) or moieties susceptible to formation of free radicals (e.g. alpha-hydrogens to hydroxyl groups in polyhydroxy polymer supports) or either of these moieties may be introduced as described below. The initiation of radical polymerization may be accomplished by irradiation or by thermal/chemical initiation using one of many known initiation systems such as e.g. peroxide initiators, azo initiators, persulphate, hydrogen peroxide, cerium(IV) salts, photoinitiators, redox systems. ATRP etc.

In certain embodiments step c) is performed under conditions such that copolymer chains comprising units derived from the first and second monomer are formed and covalently linked to the solid support either by copolymerization with the C=C double bonds or by initiation or chain transfer from the moieties susceptible to free radical formation.

In some embodiments the method further comprises a step, before step a), of derivatizing the solid support with moieties comprising copolymerizable C=C double bonds or moieties susceptible to formation of free radicals. C=C double bonds can e.g. be introduced by reacting hydroxyl groups in polyhydroxy polymers with allylating reagents such as allyl halides or allyl glycidyl ether. Other examples of methods to introduce C=C double bonds include reaction of hydroxyls with electrophilic reagents such as glycidyl (meth)acrylate, vinylbenzyl chloride etc. Moieties susceptible to formation of free radicals can be e.g. a) initiator species like hydroperoxides that can be formed by gamma or E-beam irradiation in the presence of oxygen or azo initiators formed by reaction with e.g. azobiscyanopentanoic acid or b) chain transfer groups like thiols that can be introduced e.g. by reacting an epoxy-activated support with a dithiol or sulfide ions.

In certain embodiments the moieties comprising copolymerizable C=C double bonds are allyl groups, such as allyl ether groups or allyl hydroxypropyl ether groups. Allyl groups are particularly advantageous in combination with the grafting of monomers such as vinyl sulfonic acid or vinyl phosphonic acid, optionally in combination with N-vinyl amide monomers such as vinyl pyrrolidone, in that the overall copolymerization rates are well matched.

In some embodiments said moieties susceptible to formation of free radicals comprise i) chain transfer groups such as thiols or hydrogens in alpha position to hydroxyl groups or ii) initiating groups such as peroxides, hydroperoxides, persulfates or azo compounds.

As shown in the Examples, the amount of grafted polymer can be controlled by providing different concentrations of copolymerizable double bonds on the base matrix and by providing different monomer concentrations during grafting. The ionic capacity can be controlled by varying the monomer composition and by varying the amount of grafted polymer. A skilled person will realize that some routine experimentation will be needed to reach specific values with given start materials.

EXAMPLES

Methods
Method 1. Dry Weight of Beads
A 50% (v/v) slurry of the prototype suspension was added to a glass filter with a 1.00 ml chamber above the filter. The gel was then drained by vacuum suction, and when a dry surface was spotted the gel was sucked dry for another 30 s. 1 ml of the drained gel was then added to a pre-weighed glass filter to be washed with 5*20 ml acetone. The glass filter was then put in an oven at 105° C. for 24 h before measuring the dry weight (four digits). Duplicate samples were measured.

Method 2. Ion Capacity
Approximately 4 ml drained gel was put on a small glass filter and was then washed several times with a total amount of 40 ml 0.5 M HCl and then several times with a total amount of 100 ml 1 mM HCl. The particles were then brought to a 1 ml cube whereupon the gel was drained by vacuum suction, and when a dry surface was spotted the gel was sucked dry for another 30 s. 1 ml of the drained gel was then added to a 40 ml beaker together with 20 ml of distilled water. The hydrogen ion capacity of ml 1 gel was then determined by titration.

Method 3. Allyl Content
50% slurry of the prototype suspension was added to a 1 ml cube. The gel was then drained by vacuum suction, and when a dry surface was spotted the gel was sucked dry for another 30 s. 1 ml of the drained gel was then added to a 250 ml e-flask with a vacuum fitting, together with additional 5 ml water. The suspension was then stirred with a magnetic stirrer under vacuum suction while adding saturated bromine water to the suspension. The mixture was then stirred under vacuum suction to remove excess bromine for 30 min before adding the mixture to a 30 ml titration cup. The mixture was then titrated with respect to bromide ions using silver nitrate.

Example 1. Grafting of 1-vinyl-2-pyrrolidone (VP) and Vinyl Sulfonic Acid (VSA)

1 a) Allylation of Agarose Bead Support
50 g drained agarose beads of high rigidity (prepared according to the methods described in U.S. Pat. No. 6,602,990) were added to a 500 ml round-bottom flask and 101.4 g of 50% aqueous NaOH and 77.04 g distilled water were mixed in by stirring. The temperature was raised to 50° C. for 30 minutes. Thereafter allylglycidylether (AGE), was added in an amount producing the AGF/reaction volume ratio according to Table 2, and the reaction was continued overnight for 17 hours at 50° C. The beads were then filtered off and washed with ethanol 5×300 ml and then distilled water, 5×300 ml.

Agarose beads of four different pore sizes were used, corresponding to Kd values for dextran Mw 110 kDa of 0.50, 0.67, 0.77 and 0.80. The Kd evaluation was carried out using an AKTA™ explorer equipped with an A-900 autosampler. A Shimadzu RI-detector (RID-bA) was connected to the AKTA™ system for detection of the dextran samples. The following conditions were used: Flow: 0, 2 ml/min Mobile phase: 0.2M NaCl Sample volume: 100 microliters. The dextran peaks were evaluated according to well-known methods in this field. The Kd values were then calculated as a measure of available pore surface as follows: Kd=(Ve−V0)/(Vc−V0−Vgel matrix)=(Ve−V0)/(Vt−V0). Ve=retention volume eluted dextran (ml) V0=void volume retention of raw dextran void marker) (ml), Vc=calculated column volume (bed height (cm)×surface area column (cm2)) (ml), Vt=total liquid volume (retention volume NaCl) (ml).

Some grafted prototypes were also evaluated with respect to the Kd value for dextran Mw 110 kD, using the same method. The Kd values were in these cases generally lower than for the non-grafted support beads due to the pore-filling effect of the grafted polymer chains.

1 b) Grafting
The α,α, Azodiisobutyramidine di hydrochloride (ADBA) initiator was added to a 40 ml glass vial whereupon 17 g drained allylated beads added. Distilled water, VP and aqueous VSA solution were then added to the vial. The vial was closed with a plastic top and then put in a heated shaking equipment where the vial was shaken at r.t. for 5 min before raising the temperature to 55 C. The polymerisation reactions proceeded for 17 h overnight and the particles was then washed on a glass filter with 8 gel volumes (GV) of distilled water, 8 GV of 99.5% ethanol and then 8 GV of water.

TABLE 1

VP-VSA grafting conditions

| Grafting recipe | Slurry concentration [w/w %] | mol/kg slurry mol/kg | Initiator concentration [% w/w on monomers] | Temperature | % mol VSA/ (VP + VSA) |
|---|---|---|---|---|---|
| G1 | 45 | 1.75 | 0.962 | 55 | 62 |
| G2* | 45 | 1.75 | 0.962 | 55 | 62 |
| G3 | 20 | 2.55 | 0.962 | 55 | 62 |
| G4 | 13 | 2.55 | 0.962 | 55 | 70 |

*G2: the gel was washed three times with VSA solution before the vacuum drained gel was added to the vial

TABLE 2

VP-VSA grafted prototypes

| Prototype | AGE ratio [v/v] | Kd dx 110K Base matrix | Particle size [micrometers] | Allyl level [micromol/ml] | Amount of graft polymer [mg/ml] | Ionic capacity [micromol/ml] |
|---|---|---|---|---|---|---|
| S50-G1-A50 | 0.5 | 0.5 | 41 | 26 | — | — |
| S50-G1-A25 | 0.25 | 0.5 | 41 | 22 | 3 | 27 |
| S50-G2-A200 | 2 | 0.5 | 41 | 31 | — | 75 |
| S50-G3-A25 | 0.25 | 0.5 | 41 | 19 | — | 28 |
| S50-G4-A200 | 2 | 0.5 | 41 | 31 | — | 76 |
| S67-G1-A450 | 4.5 | 0.67 | 51 | 44 | — | 73 |
| S67-G1-A200 | 2 | 0.67 | 51 | 31 | — | 47 |
| S67-G1-A100 | 1 | 0.67 | 51 | 21 | — | 24 |
| S77-G1-A450 | 4.5 | 0.77 | 64 | 38 | 12 | 60 |
| S77-G1-A200 | 2 | 0.77 | 64 | 25 | 6 | 39 |
| S80-G1-A200 | 2 | 0.8 | 65 | 31 | 3 | 37 |

Prototype S67-G1-A200 had a Kd value of 0.295 for dextran 110 kD and the reference Fractogel® EMD SE Hicap (Merck) had a corresponding value of 0.093.

Example 2. Evaluation of Prototypes Grafted with VP and VSA

Column Packing and Testing

The prototype media were settled and compressed in Tricorn 5/50 columns. After packing, the columns were tested in 0.4 M NaCl at 0.065 ml/min by injecting 10 µl of 2 M NaCl containing 3% (v/v) acetone. $A_{288}$, $A_{268}$ and conductivity peaks were registered and integrated. The acceptance criteria for a successful packing was an asymmetry value between 0.8 and 1.5.

Mab Sample Preparation

Protein A purified Mab was buffer-exchanged with a HiPrep Desalting 26/10 column to 50 mM Na-acetate+10 mM NaCl pH 5.25. Protein concentration was then determined by spectrophotometry.

Concentration Determination by $A_{280}$

The protein concentration was determined by spectrophotometry at 280 nm using Lambert-Beers law (Equation 1).

$$C = A/(1*\varepsilon)$$ Equation 1:

where C is concentration (mg/ml), 1 is the path length (cm) and $\varepsilon$ is the absorptivity at 1 g/ml, deduced from the molar extinction coefficient.

Chromatography

The sample was applied with a superloop to a pre-equilibrated column at a load of 50 mg/ml media. The column was then washed, eluted with a NaCl gradient, stripped (=regenerated), cleaned with 1 M NaOH and finally re-equilibrated (Table 3). All runs were performed on an ÄKTA explorer 100 system with Unicorn 5.11 as control software. The prototypes and reference media were tested with the same start and elution buffers to achieve the same gradient length and slope. Therefore, the start buffers (both acetate and phosphate) were supplied with 10 mM NaCl to diminish the possible non-traditional behavior.

The start sample, FT and collected fractions were analyzed by SEC and in selected cases by HCP analysis (Gyrolab).

TABLE 3

Selectivity method overview

| Step | Flow rate (ml/min) | Volume (CV) | Comment |
|---|---|---|---|
| Equilibration | 1 | 1 | 50 mM Na-acetate + 10 mM NaCl, pH 5.25 |
| Sample injection | 0.25 | Variable | Depending on protein concentration. Collection of flow-through. |
| Wash | 0.25 | 5 | 50 mM Na-acetate + 10 mM NaCl, pH 5.25 |
| Gradient elution | 0.25 | 20 | 0-350 mM NaCl with same buffer |
| Strip | 0.25 | 10 | 50 mM Na-acetate pH 5.25 + 500 mM NaCl |
| CIP | 1 | 3 | 1M NaOH |
| Re-equilibration | 1 | 12 | 50 mM Na-acetate + 10 mM NaCl, pH 5.25 |

SEC Analysis

Monomer purity was assessed by size exclusion chromatography (SEC) using two Superdex™ 200 5/150 GL columns connected in series. The mobile phase was phosphate buffered saline (PBS) and the flow rate was 0.35 ml/min for 15 min (8 minutes for prototypes). Ten microliters of each sample was applied to the columns. The analyses were performed on an ÄKTA explorer 10 system with Unicorn 5.11 as control software.

SEC was also used for monomer concentration determination. Essentially, the monomer concentration was determined by correlating the monomer area of the sample to the monomer area of the start sample. First, the monomer start concentration was determined (Equation 2)

$$C_{monomer\ start} = C_{total\ start} * \text{monomer purity}$$ Equation 2:

where the $C_{total\ start}$ is obtained in the concentration determination by $A_{280}$ and the monomer purity is obtained by the SEC purity determination. Then, the monomer concentration of the sample can be calculated by using Equation 3.

$$C_{monomer\ sample} = \text{Area}_{monomer\ sample} / \text{Area}_{monomer\ start} * C_{monomer\ start}$$ Equation 3:

where the monomer areas are obtained by integrating the monomer peak in the SEC analysis.

HCP Analysis

HCP levels were measured using commercial anti-CHO HCP antibodies (Cygnus Technologies). Essentially, an ELISA method was adapted to a Gyrolab Workstation LIF (Gyros AB) using Gyrolab Bioaffy 200 HC microlaboratory discs.

Presentation of Data

Figure 2:
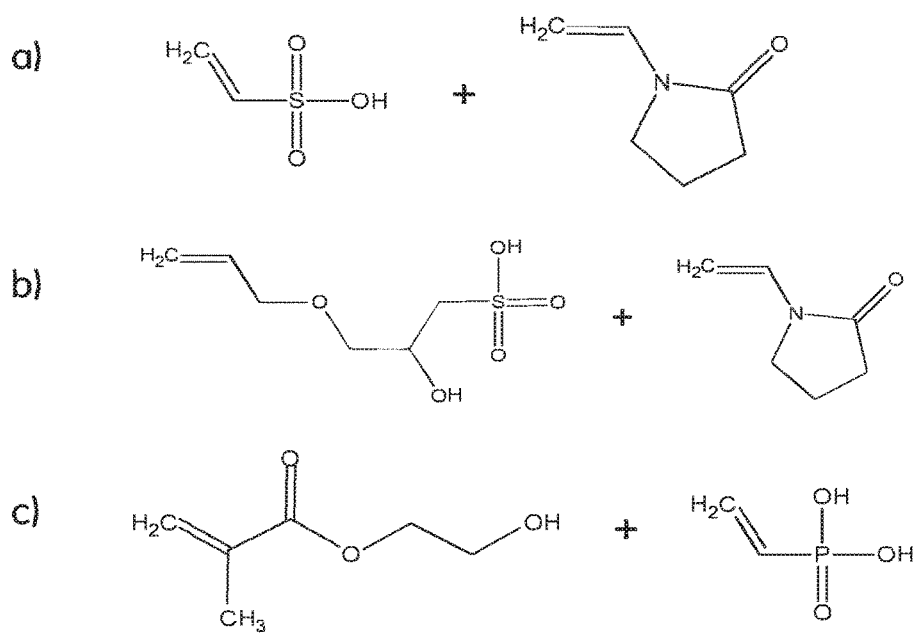
FIG. 2 shows mixtures of monomers used for grafting: a) vinyl sulfonic acid (VSA) and vinylpyrrolidone (VP), b) 2-hydroxy-1-propanesulfonic acid (APS) and vinylpyrrolidone and c) hydroxyethylmethacrylate (HEMA) and vinylphosphonic acid (VPA).
Figure 3:
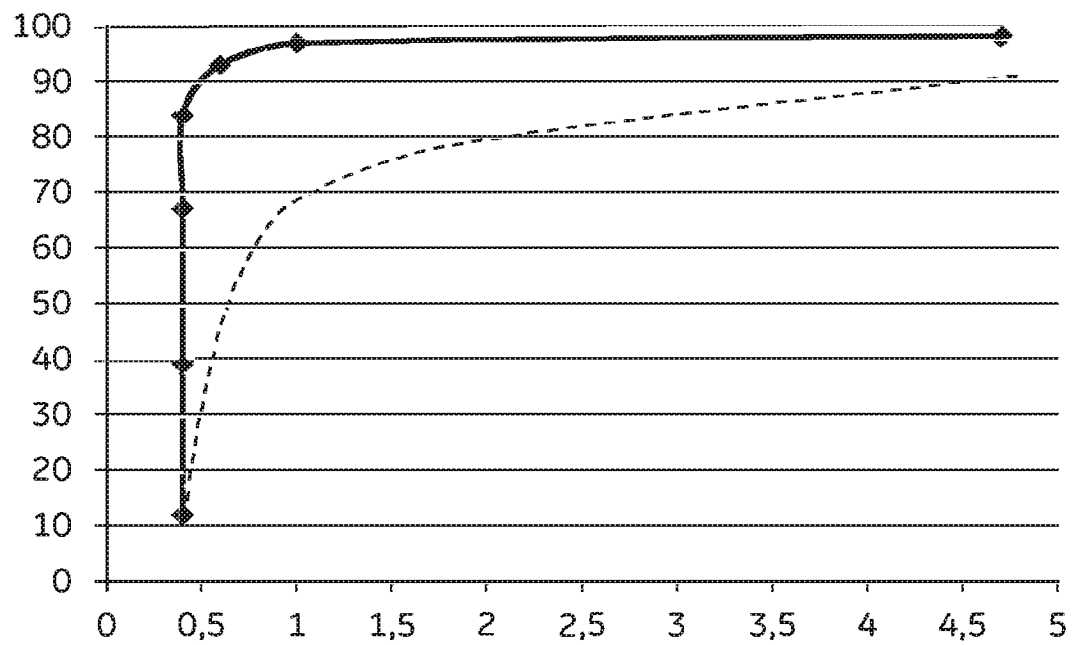
FIG. 3 shows an idea (solid line) selectivity curve for removal of aggregated antibodies and a less than ideal (dotted line) curve.
Figure 4:
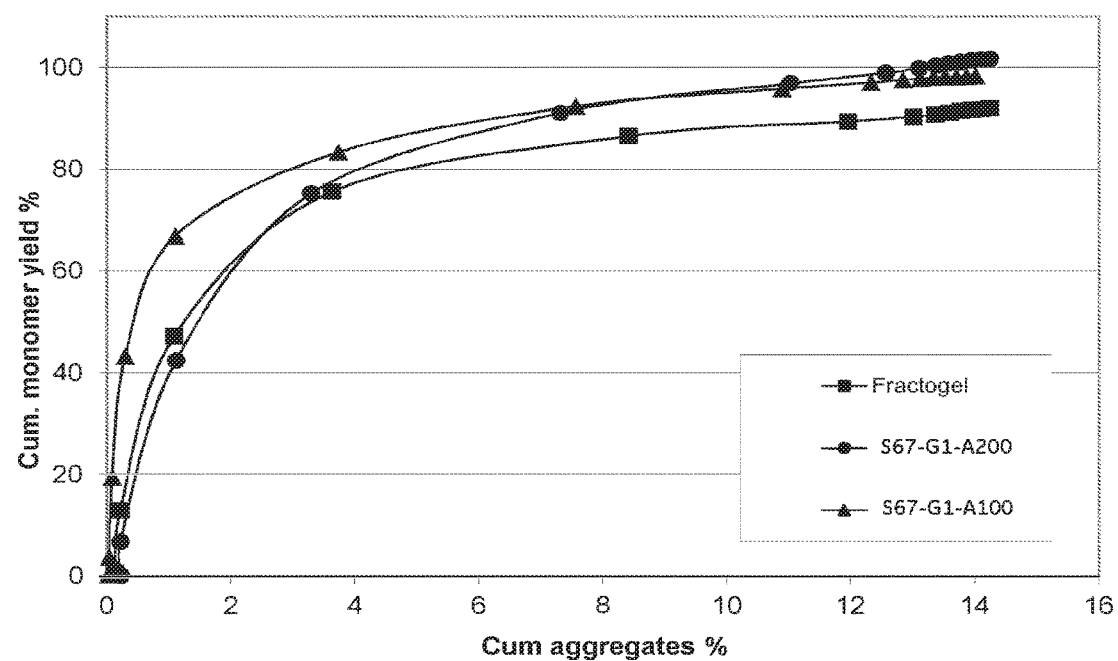
FIG. 4 shows aggregate removal selectivity curves for VP-VSA prototypes S67-G1-A100 and S67-G1-A200 compared with a reference.
Figure 5:
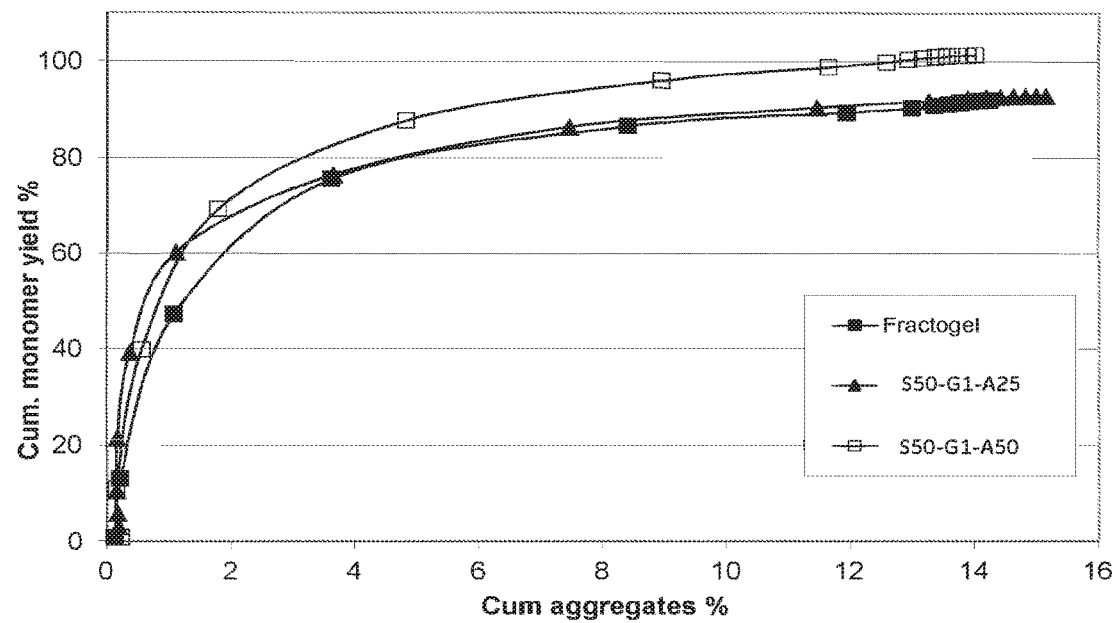
FIG. 5 shows aggregate removal selectivity curves for VP-VSA prototypes S50-G1-A25 and S50-G1-A50 compared with a reference.
Figure 6:
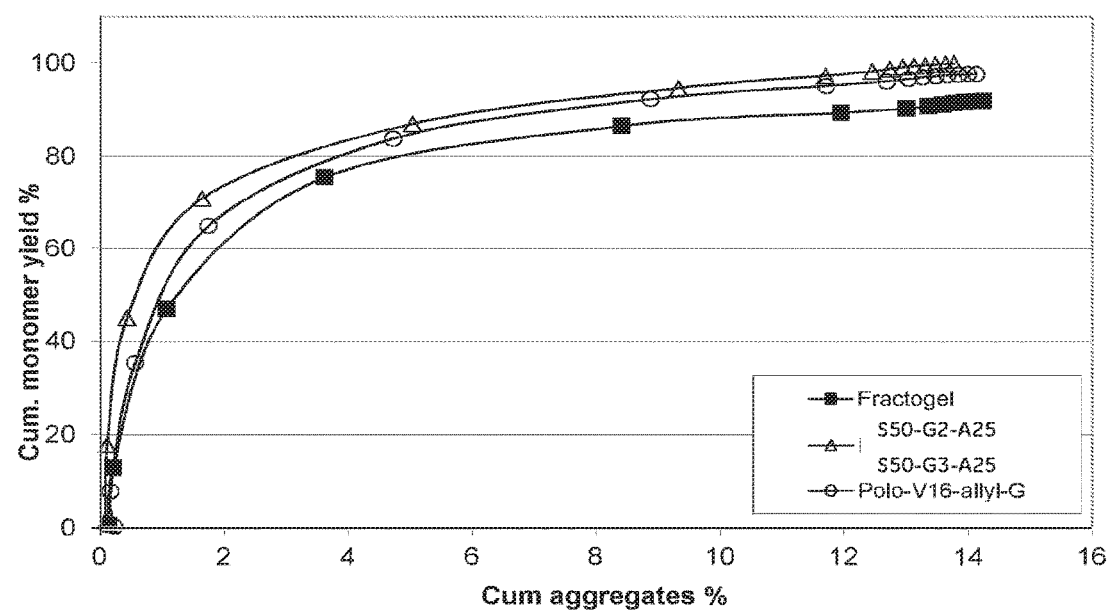
FIG. 6 shows aggregate removal selectivity curves for VP-VSA prototypes S50-G2-A25 and S50-G3-A25 compared with a reference.
Figure 7:
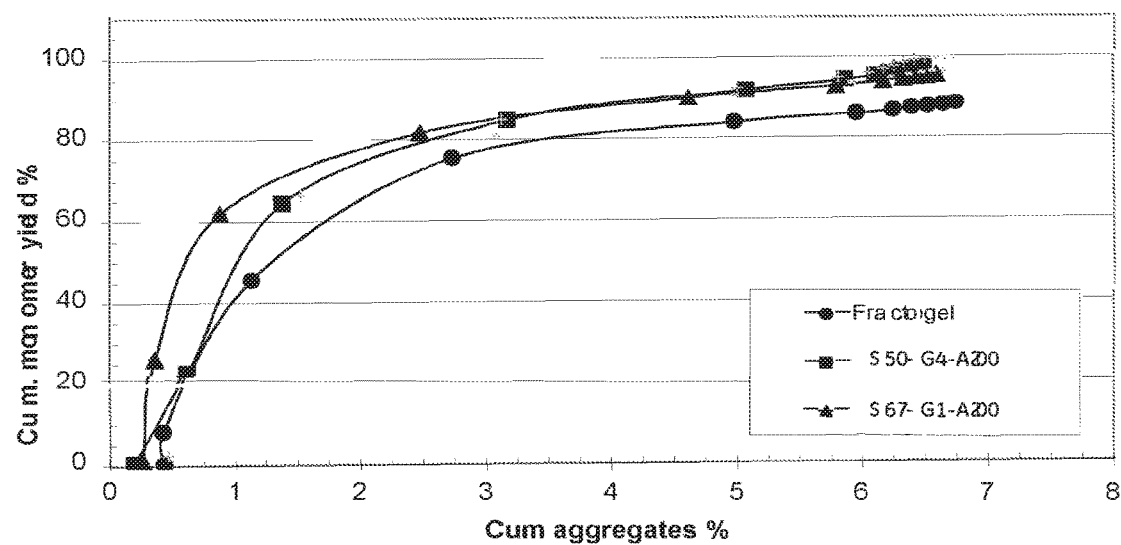
FIG. 7 shows aggregate removal selectivity curves for VP-VSA prototypes S50-G4-A200 and S67-G1-A200 compared with a reference. The initial aggregate concentration was 7%.
Figure 8:
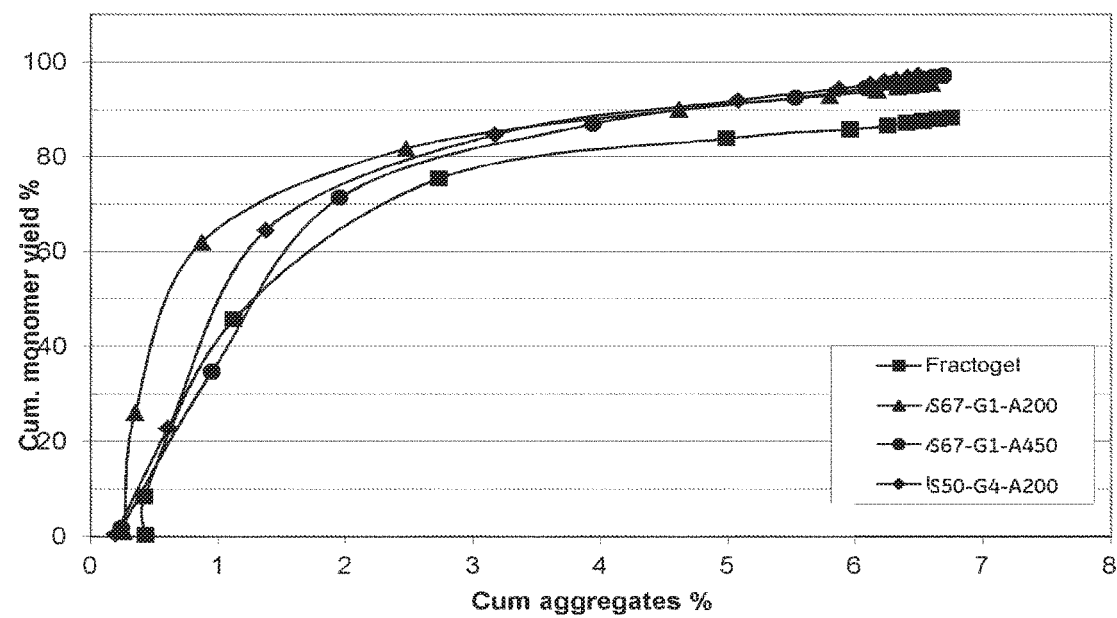
FIG. 8 shows aggregate removal selectivity curves for VP-VSA prototypes S67-G1-A200, S67-G1-A450 and S50-G4-A200 compared with a reference The initial aggregate concentration was 7%.
Figure 9:
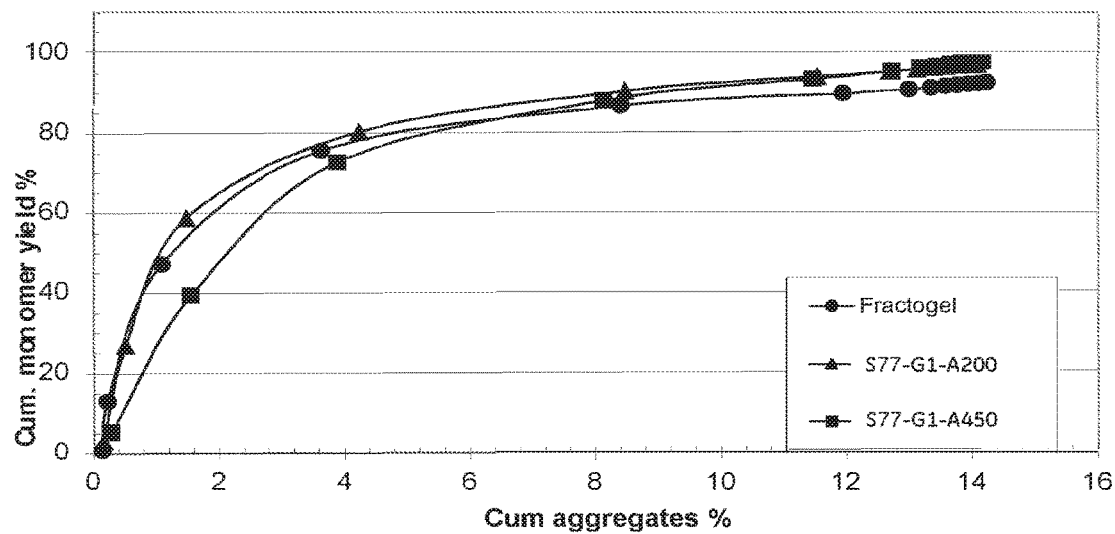
FIG. 9 shows aggregate removal selectivity curves for VP-VSA prototypes S77-G1-A200 and S77-G1-A450 compared with a reference.
Figure 10:
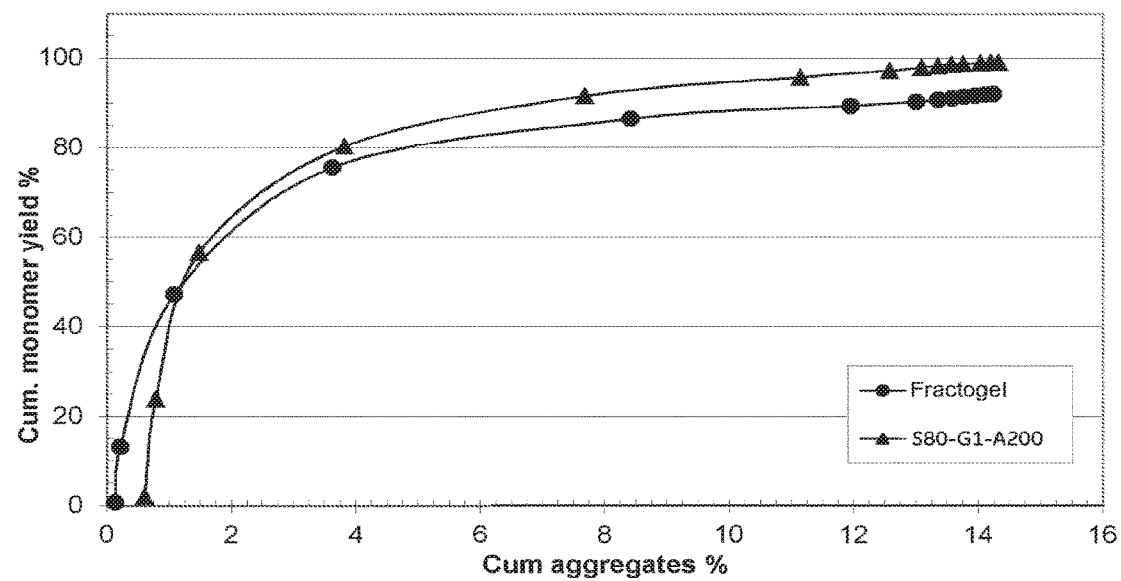
FIG. 10 shows an aggregate removal selectivity curve for VP-VSA prototype S80-G1-A200 compared with a reference.

The collected fractions were analysed (SEC) with respect to monomer concentration and aggregate concentration. From these data, the cumulative monomer yield in fractions 1 to x and the cumulative aggregate content in the same fractions could be calculated. When the cumulative monomer yield is plotted vs the cumulative aggregate content, curves as in FIG. 2 are obtained, FIG. 2 depicts an idealized curve, where most of the aggregates are removed at a high monomer yield. The experimental curves (exemplified in FIG. 2 with a dotted line) will in general show lower cumulative yields and the better selectivity a prototype has, the higher the cumulative yield values for each cumulative aggregate value will be. In the presentations of selectivity curves, data derived from Fractogel® EMD SE Hicap (Merck) have been used as reference curves. The sulfoethyl groups of this cation exchange matrix are located on grafted polymer chains and the matrix is recommended for removal of aggregates in antibody processing.

pH Choice

An optimization of the pH was done to find a suitable pH for these runs. A representative prototype was tested at pH 4.75, 5.0 and 5.25, with best result at pH 5.25. Two reference media, Capto® SP ImpRes (GE Healthcare) and Fractogel® EMD SE Hicap (Merck), were run at two different pH values: 5.0 and 5.25. The separation of aggregates from monomer was better at the higher pH. Moreover, a third peak, thought to be composed of precipitated antibody, was almost absent at pH 5.25. Hence, all media were run in a gradient from 50 mM Na-acetate+10 mM NaCl pH 5.25 to 50 mM Na-acetate+500 mM NaCl pH 5.25. The NaCl was included to diminish/eliminate non-traditional behavior.

Dynamic Binding Capacitates (DBC)

Column Packing and Testing

The prototype media were settled and compressed in Tricorn 5/50 columns at 4 ml/min using 0.2 M NaCl+20% ethanol as mobile phase.

After packing the columns were tested in 0.4 M NaCl at 0.25 ml/min by injection of 20 µl 1 M NaCl containing 3% (v/v) acetone. Both $A_{280}$, $A_{260}$ and conductivity peaks were registered and integrated but the conductivity values were the ones reported. The acceptance criteria for a successful packing was an asymmetry value between 0.8 and 1.5.

Sample Preparation

MAb eluate (~24 mg/mL) was buffer exchanged by using a HiPrep Desalting 26/10 column, giving a concentration of approximately 15 mg/ml with 50 mM acetate buffer pH 5.25.

The sample was then diluted to a concentration of 3.7-3.8 mg/ml.

The concentration for the sample solution was determined by measuring UV at 280 nm and calculated using Lambert Beer law and the extinction coefficient 1.5

DBC Method

After equilibration the sample was applied (4 min residence time) with a super loop until 85% of the maximum absorbance was reached. The media was then washed, eluted, regenerated and CIPped (cleaned) with 0.5 M NaOH and finally re-equilibrated. The DBC (Qb 10%) was then calculated from the chromatogram at 280 nm.

The DBC values for the VP-VSA prototypes and Fractogel EMD SE Hicap are shown in Table 4.

TABLE 4

Dynamic binding capacities for IgG (monoclonal).

| Prototype | DBC (mg/ml) |
| --- | --- |
| S50-G1-A50 | 81 |
| S50-G1-A25 | 60 |
| S50-G2-A200 | 70 |

TABLE 4-continued

Dynamic binding capacities for IgG (monoclonal).

| Prototype | DBC (mg/ml) |
| --- | --- |
| S50-G3-A25 | 86 |
| S50-G4-A200 | 121 |
| S67-G1-A450 | 138 |
| S67-G1-A200 | 125 |
| S67-G1-A100 | 70 |
| S77-G1-A450 | 124 |
| S77-G1-A200 | 96 |
| S80-G1-A200 | 90 |
| Fractogel EMD SE Hicap | 119 |

Aggregate Removal

The aggregate removal selectivity for the VP-VSA prototypes in comparison with the reference Fractogel EMD SE Hicap is shown in FIGS. 4-10. The best selectivities are obtained with prototypes prepared with low allyl contents, but a trade-off has to be made with respect to DBC. Increasing the pore size of the matrices had a positive effect and particularly good results were obtained with supports having a Kd of 0.67-0.80 for dextran of Mw 110 kDa.

Prototypes with Polystyrene Base Matrices

Figure 11:
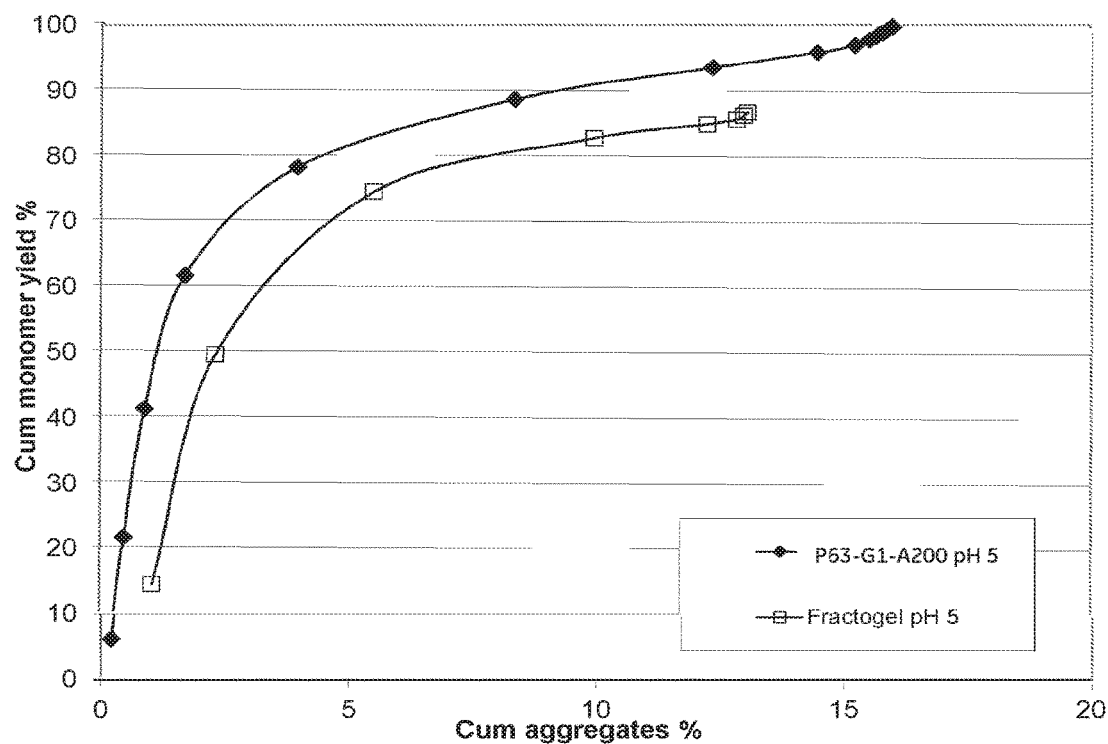
FIG. 11 shows an aggregate removal selectivity curve for polydivinylbenzene-based VP-VSA prototype P63-G1-A200 at pH 5.0 compared with a reference.
Figure 12:
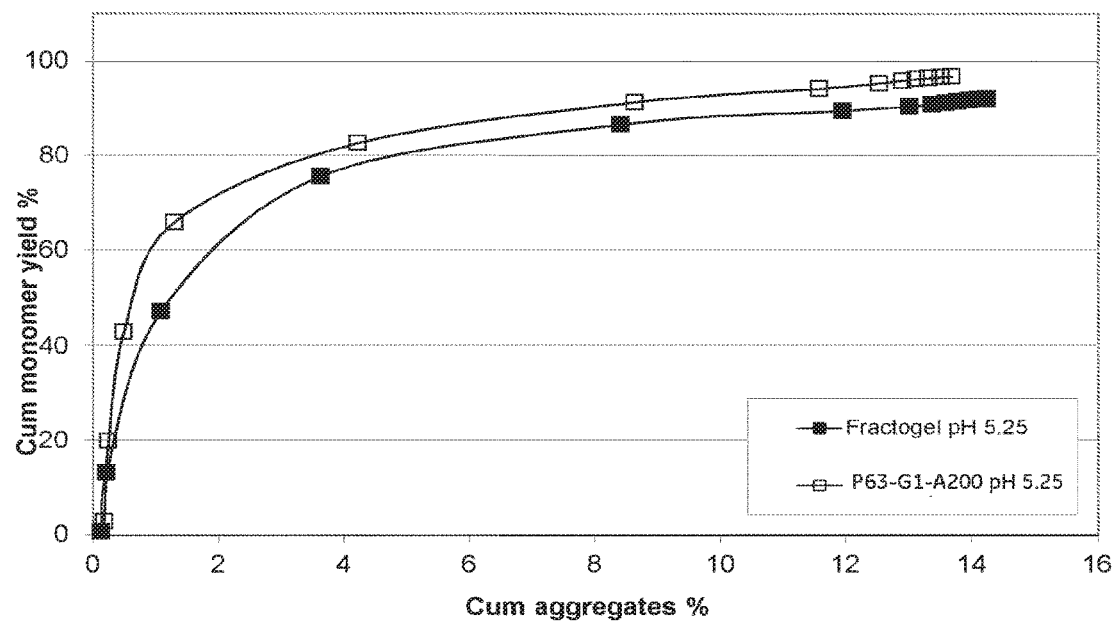
FIG. 12 shows an aggregate removal selectivity curve for polydivinylbenzene-based VP-VSA prototype P63-G1-A200 at pH 5.25 compared with a reference.

A high selectivity was also found when using prototype P63-G1-A2 which was based on a polydivinyl benzene (DVB) base matrix, and the DBC for this prototype was 86 mg/ml. This prototype was made from 40 micrometer polydivinylbenzene beads with a pore size corresponding to a Kd value of 0.63 for dextran of Mw 110 kDa. The beads had been hydroxylated according to the methods described in U.S. Pat. No. 6,420,028, allylated according to the methods above, with an AGE ratio of 2 and finally grafted with vinylpyrrolidone (VP) and vinylsulfonic acid (VSA) according to recipe G4 to give an ionic capacity of 66 micromol/ml. The aggregate removal results for these beads are shown in FIGS. 11 and 12.

Example 3. Grafting of VP and 3-allyloxy,2-hydroxy-1-propanesulfonic Acid (APS)

Agarose beads were washed on a glass filter with 40% APS solution (2× gel volume) several times. The suspension was sucked dry whereupon 75 g was added to a 250 ml three necked round bottom flask. 1.5 g of ADBA was added to the flask together with 30 g of the APS solution and 25.5 ml VP. The polymerisation was started at 65° C. and was stirred for approximately 17 h. The gel was washed thoroughly with distilled water.

Measurement of static binding capacities in 96 well filter plates

1% gel slurries were prepared and filled into a 96 well filter plate, corresponding to 2 microliters settled gel/well, using a pre-programmed Gilson robot.

Equilibration of the gels filled in the plate was performed by addition of 200 microliters equilibration buffers from the plate prepared in the Tecan robot, followed by agitation at 1100 rpm for 1 minute, after which the buffer was removed by vacuum suction. The equilibration step was performed three times and after the last equilibration the buffer was removed with centrifugation.

200 µl sample prepared in each buffer was added to each well followed by agitation for 180 minutes. The unbound sample was collected into a UV-plate by centrifugation, and the absorbance was recorded at four wavelengths (254, 280, 290 and 310 nm) by reading the plate in the Spectra Max plate reader. A calibration curve was made by diluting one of the starting solutions. The amount of bound sample per mL gel was calculated by using the Assist software.

The synthesis conditions, the amount of grafted polymer and the ionic capacity are listed in Table 5 and the static binding capacity of polyclonal IgG on the prototypes is listed in Table 6.

TABLE 5

APS grafting conditions

| Prototype | Amount of allyl groups [µmol/mL] | IEX monomer | Co-monomer | Molar ratio IEX/Co-monomer | APS (40%) | Co-monomer | Water | ADBA [mg] | Amount of graft polymer [mg/mL] | Ionic capacity [µmol/mL] |
|---|---|---|---|---|---|---|---|---|---|---|
| APS1 | 197 | APS | VP | 1:1 | 15 | 3.1 | — | 300 | 27 | 40 |
| APS2 | 197 | APS | VP | 1:4 | 6 | 4.9 | 6 | 300 | 56 | 60 |
| APS3 | 194 | APS | VP | 1:8 | 3.33 | 5.43 | 8.4 | 300 | 52 | 57 |
| APS4 | 164 | APS | HEMA | 5:1 | 15 | 0.72 | — | 180 | 16 | 21 |
| APS5 | 164 | APS | HEMA | 10:1 | 15 | 0.36 | — | 160 | 8 | 18 |
| APS6 | 252 | APS | VP | 1:1 | 15 | 3.32 | — | 300 | 28 | 48 |
| APS7 | 252 | APS | VP | 1:4 | 6 | 5.30 | 6 | 300 | 60 | 70 |
| APS8 | 252 | APS | VP | 1:8 | 1.3 | 5.43 | 8.4 | 300 | 71 | 69 |
| APS9 | 275 | APS | VP | 1:4 | 6 | 5.30 | 6 | 300 | 61 | 74 |
| APS10 | 325 | APS | VP | 1:4 | 6 | 5.30 | 6 | 300 | 63 | 77 |

TABLE 6

Evaluation of APS grafted prototypes

| Prototype | IEX monomer | Co-monomer | Molar ratio IEX/Co-monomer | Amount of graft polymer [mg/mL] | Ionic capacity [µmol/mL] | SBC polyclonal IgG 0 mM NaCl | 30 mM NaCl | 50 mM NaCl | 100 mM NaCl |
|---|---|---|---|---|---|---|---|---|---|
| APS1 | APS | VP | 1:1 | 27 | 40 | 102 | 91 | 88 | 54 |
| APS2 | APS | VP | 1:4 | 56 | 60 | 150 | 113 | 94 | 29 |
| APS3 | APS | VP | 1:8 | 52 | 57 | 149 | 120 | 108 | 61 |
| APS4 | APS | HEMA | 5:1 | 16 | 21 | 51 | 49 | 41 | 27 |
| APS5 | APS | HEMA | 10:1 | 8 | 18 | 40 | 34 | 27 | 11 |
| APS6 | APS | VP | 1:1 | 28 | 48 | 98 | 103 | 97 | 57 |
| APS7 | APS | VP | 1:4 | 60 | 70 | 162 | 125 | 110 | 56 |
| APS8 | APS | VP | 1:8 | 71 | 69 | 168 | 125 | 111 | −5 |
| APS9 | APS | VP | 1:4 | 61 | 74 | 158 | 142 | 113 | 58 |
| APS10 | APS | VP | 1:4 | 63 | 77 | 139 | 130 | 109 | 57 |

Example 4. Grafting of VSA

Allylated agarose beads were washed on a glass filter with a 30% VSA solution (2× gel volume) several times. The suspension was sucked dry whereupon 75 g was added to a 250 ml round bottom flask. 0.95 g of ADBA was then added to the flask together with 75 g of the VSA solution. The polymerisation started by shaking at 65° C. for approximately 17 h. The gel was then washed thoroughly with distilled water. The synthesis conditions, the amount of grafted polymer and the ionic capacity are listed in Table 7 and the static binding capacity of polyclonal IgG on the prototypes is listed in Table 8.

TABLE 7

VSA grafting conditions.

| Prototype | Amount of allyl groups [µmol/mL] | IEX monomer | VSA (30%) | Co-monomer | Water | ADBA [mg] | Amount of graft polymer [mg/mL] | Ionic capacity [µmol/mL] |
|---|---|---|---|---|---|---|---|---|
| VSA1 | 197 | VSA | 15 | — | — | 190 | 17 | 99 |
| VSA2 | 337 | VSA | 15 | — | 2 | 190 | 16 | 118 |
| VSA3 | 337 | VSA | 15 | — | 2 | 95 | 16 | 118 |
| VSA4 | 252 | VSA | 15 | — | — | 190 | 24 | 152 |
| VSA5 | 275 | VSA | 15 | — | — | 190 | | 160 |
| VSA6 | 325 | VSA | 15 | — | — | 190 | 24 | 163 |

TABLE 8

Evaluation of VSA grafted prototypes.

| Prototype | IEX monomer | Co-monomer | Amount of graft polymer [mg/mL] | Ionic capacity [µmol/mL] | SBC polyclonal IgG | | | |
|---|---|---|---|---|---|---|---|---|
| | | | | | 0 mM NaCl | 30 mM NaCl | 50 mM NaCl | 100 mM NaCl |
| VSA1 | VSA | — | 17 | 99 | 97 | 97 | 76 | 58 |
| VSA2 | VSA | — | 16 | 118 | 84 | 90 | 82 | 64 |
| VSA3 | VSA | — | 16 | 118 | 80 | 79 | 83 | 62 |
| VSA4 | VSA | — | 24 | 152 | 75 | 85 | 92 | 90 |
| VSA5 | VSA | — | | 160 | 49 | 80 | 90 | 87 |
| VSA6 | VSA | — | 24 | 163 | 29 | 59 | 70 | 78 |

Example 5. Grafting of Hydroxyethylmethacrylate (HEMA) and Vinylphosphonic acid (VPA)

The ADBA initiator was added to a 30 ml glass vial whereupon 15 g of dry sucked gel (pre-washed with 40% APS) was added. Distilled water, the neutral monomer and the ionic monomer solution were then added to the vial. The vial were closed with a plastic top and then put in a heat-shaking equipment where the vials were shaken in r.t. for 5 min before raising the temperature to 55 C. The polymerisation reactions proceeded for 17 h over night and the particles was then put on a glass filter to be washed with 8× gel volume of distilled water, 8× gel volume of 99.5% ethanol and then 8× gel volume of water. The synthesis conditions, the amount of grafted polymer and the ionic capacity are listed in Table 9 and the static binding capacity of polyclonal IgG on the prototypes is listed in Table 10.

TABLE 9

VPA grafting conditions.

| Prototype | Amount of allyl groups [µmol/mL] | IEX monomer | Co-monomer | Molar ratio IEX/Co-monomer | Amounts [g] | | | ACBA [mg] | Amount of graft polymer [mg/mL] | Ionic capacity [µmol/mL] |
|---|---|---|---|---|---|---|---|---|---|---|
| | | | | | VPA | Co-monomer | Water | | | |
| VPA1 | 197 | VPA | — | | 6 | — | 9 | 300 | 16 | 188 |
| VPA2 | 164 | VPA | — | | 9 | — | 6 | 450 | 32 | 260 |
| VPA3 | 164 | VPA | — | | 9 | — | 6 | 230 | 29 | 233 |
| VPA4 | 337 | VPA | — | | 9 | — | 6 | 450 | 25 | 313 |
| VPA5 | 197 | VPA | VP | 1:1 | 4.8 | 4.9 | 10.2 | 370 | 0.1 | 59 |
| VPA6 | 197 | VPA | VP | 1:4 | 1.9 | 7.9 | 7.5 | 370 | 16 | 45 |
| VPA7 | 164 | VPA | HEMA | 5:1 | 4.8 | 1.15 | 7.2 | 210 | 31 | 148 |
| VPA8 | 164 | VPA | HEMA | 10:1 | 4.8 | 0.58 | 7.2 | 200 | 17 | 144 |
| VPA9 | 252 | VPA | — | | 6 | — | 9 | 300 | 23 | 233 |
| VPA10 | 252 | VPA | HEMA | 10:1 | 4.8 | 0.58 | 2.5 | 200 | 26 | 195 |

TABLE 10

Evaluation of VPA grafted prototypes

| Prototype | IEX monomer | Co-monomer | Molar ratio IEX/Co-monomer | Amount of graft polymer [mg/mL] | Ionic capacity [µmol/mL] | SBC polyclonal IgG | | | |
|---|---|---|---|---|---|---|---|---|---|
| | | | | | | 0 mM NaCl | 30 mM NaCl | 50 mM NaCl | 100 mM NaCl |
| VPA1 | VPA | n.a | n.a | 16 | 188 | 98 | 88 | 90 | 70 |
| VPA2 | VPA | n.a | n.a | 32 | 260 | 72 | 96 | 98 | 97 |
| VPA3 | VPA | n.a | n.a | 29 | 233 | 54 | 82 | 99 | 88 |
| VPA4 | VPA | n.a | n.a | 25 | 313 | 54 | 84 | 95 | 94 |
| VPA5 | VPA | VP | 1:1 | 0.1 | 59 | 69 | 62 | 57 | 48 |
| VPA6 | VPA | VP | 1:4 | 16 | 45 | 55 | 50 | 46 | 40 |
| VPA7 | VPA | HEMA | 5:1 | 31 | 148 | 86 | 105 | 100 | 91 |
| VPA8 | VPA | HEMA | 10:1 | 17 | 144 | 94 | 102 | 106 | 78 |
| VPA9 | VPA | n.a | n.a | 23 | 233 | 73 | 85 | 88 | 70 |
| VPA10 | VPA | HEMA | 1:10 | 26 | 195 | 65 | 84 | 99 | 79 |

The VPA and VPA/HEMA grafted prototypes are remarkably insensitive to the salt concentration—going from 0 to 100 ml NaCl, only 10-20% of the binding capacity is lost. Also, as shown in FIG. 13b) the prototype VPA1 was able to resolve the proteins lysozyme and cytochrome C which was not possible with the reference media SP Sepharose HP (GE Healthcare) shown in FIG. 13a). The prototype VPA2 gave a selectivity very similar to VPA1. In the selectivity test, a mixture of the test proteins lysozyme, cytochrome C and ribonuclease A was injected and eluted with a salt gradient. A monoclonal antibody was also injected separately and eluted under the same conditions.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. It should be noted that features from different embodiments and aspects can be combined to create further embodiments.

All publications, patent publications, and patents are herein incorporated by reference to the same extent as if each individual publication or patent was specifically and individually indicated to be incorporated by reference.

The invention claimed is:

1. A separation matrix comprising a solid support and copolymer chains bound to said solid support, wherein said copolymer chains comprise units derived from
    a) a first monomer of structure $CH_2=CH-L-X$, where L is a covalent bond or an alkyl ether or hydroxysubstituted alkyl ether chain comprising 2-6 carbon atoms, and X is a sulfonate group and
    b) an N-vinyl amide,
    wherein the molar ratio of the units derived from the first monomer to the units derived from the second non-charged monomer is 0.05 to 5.

2. The separation matrix of claim 1, wherein said first monomer is selected from a group consisting of vinyl sulfonate and allyloxyhydroxypropyl sulfonate.

3. The separation matrix of claim 1, wherein said first monomer is vinyl sulfonate.

4. The separation matrix of claim 1, wherein said second non-charged monomer is selected from a group consisting of N-vinyl pyrrolidone, N-vinyl caprolactam, N-vinyl formamide and N-vinyl acetamide.

5. The separation matrix of claim 1, wherein said second non-charged monomer is N-vinyl pyrrolidone.

6. The separation matrix of claim 1, wherein in said copolymer chains the molar ratio of the units derived from the first monomer to the units derived from the second non-charged monomer is 0.5 to 2.

7. The separation matrix of claim 1, having an ion capacity of 20-200 micromol/mL and a pore size corresponding to a KD value of 0.1-0.8, measured with dextran of Mw 110 kDa as the probe molecule.

8. The separation matrix of claim 7, wherein the ion capacity of said matrix is 30-70 micromol/mL.

9. The separation matrix of claim 1, wherein the total content of said copolymer chains in the matrix is 2-80 mg/ml.

10. The separation matrix of claim 1, wherein said solid support comprises a polysaccharide having has a pore size corresponding to a KD value of 0.5-0.9, measured with dextran of Mw 110 kDa as the probe molecule.

11. The separation of claim 1, wherein said solid support comprises agar or agarose.

12. The separation matrix of claim 11, wherein the total content of said copolymer chains in the matrix is 2-20 mg/ml.

13. The separation matrix of claim 1, wherein said solid support comprises crosslinked agarose and wherein said separation matrix has a pore size corresponding to a KD value of 0.2-0.6, measured with dextran of Mw 110 kDa as the probe molecule.

14. A separation matrix comprising a solid support and copolymer chains bound to said solid support, wherein said copolymer chains comprise units derived from
    a) a first monomer selected from a group consisting of vinyl sulfonate and allyloxyhydroxypropyl sulfonate and
    b) a second non-charged monomer selected from the group consisting of N-vinyl pyrrolidone, N-vinyl caprolactam, N-vinyl formamide and N-vinyl acetamide,
    wherein in said copolymer chains the molar ratio of the units derived from the first monomer to the units derived from the second non-charged monomer is 0.5 to 2.

15. The separation matrix of claim 14, having an ion capacity of 30-70 micromol/mL and a pore size corresponding to a KD value of 0.1-0.8, measured with dextran of Mw 110 kDa as the probe molecule.

16. The separation matrix of claim 14, wherein the total content of said copolymer chains in the matrix is 2-20 mg/ml.

17. The separation matrix of claim 14, wherein said solid support agar or agarose having has a pore size corresponding to a KD value of 0.5-0.9, measured with dextran of Mw 110 kDa as the probe molecule.

18. The separation matrix according to claim 14, wherein said solid support comprises crosslinked agarose and wherein said separation matrix has a pore size corresponding to a KD value of 0.2-0.6, measured with dextran of Mw 110 kDa as the probe molecule.

19. The separation matrix of claim 14, wherein said solid support comprises crosslinked agarose and wherein said separation matrix has a pore size corresponding to a KD value of 0.2-0.6, measured with dextran of Mw 110 kDa as the probe molecule.

20. A separation matrix comprising a solid support and copolymer chains bound to said solid support having an ion capacity of 30-70 micromol/mL and a pore size corresponding to a KD value of 0.1-0.8, measured with dextran of Mw 110 kDa as the probe molecule, wherein said copolymer chains comprise units derived from
    a) vinyl sulfonate and b) N-vinyl pyrrolidone,
    wherein in said copolymer chains the molar ratio of the units derived from the first monomer to the units derived from the second non-charged monomer is 0.5 to 2, wherein the total content of said copolymer chains in the matrix is 2-20 mg/ml, and wherein said solid support comprises crosslinked agarose and wherein said separation matrix has a pore size corresponding to a KD value of 0.2-0.6, measured with dextran of Mw 110 kDa as the probe molecule.

* * * * *